US006979682B2

(12) United States Patent
Hunt et al.

(10) Patent No.: US 6,979,682 B2
(45) Date of Patent: Dec. 27, 2005

(54) PLATELET-ACTIVATING FACTOR ANTAGONIST INHIBITION OF ANGIOGENESIS AND TUMOR GROWTH INDUCED BY BASIC FIBROBLAST

(75) Inventors: Jay D. Hunt, Slidell, LA (US); Haydee E. Bazan, New Orleans, LA (US); Victor L. Marcheselli, Covington, LA (US); Julio Alvarez Builla Gomez, Madrid (ES); Nicholas G. Bazan, New Orleans, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 35 days.

(21) Appl. No.: 10/082,821

(22) Filed: Feb. 25, 2002

(65) Prior Publication Data

US 2002/0169158 A1    Nov. 14, 2002

Related U.S. Application Data

(60) Provisional application No. 60/271,286, filed on Feb. 23, 2001.

(51) Int. Cl.$^7$ .............................................. A61K 31/55
(52) U.S. Cl. ........................ 514/219; 514/77; 514/91; 514/218
(58) Field of Search ................................ 514/218, 219

(56) References Cited

FOREIGN PATENT DOCUMENTS

WO            01/83440            8/2001

OTHER PUBLICATIONS

Hunt, J. D. et al., "The Platelet-Activationg Factor (FAF) Antagonist BN-50730 Inhibits Antgiogenesis," Proceedings of the American Association for Cancer Research: Cell and Tumor Biology, vol. 41, abstract 4099, (2000).*
Angelov, L. et al., "Inhibition of angiogenesis by blocking activation of the vascular endothelial growth factor receptor 2 leads to decreased growth of neurogenic sarcomas," Cancer Research, vol. 59, pp. 5536-5541 (1999).
Bazan, N.G. et al., "Platelet-activating factor and retinoic acid synergistically activate the inducible prostaglandin synthase gene," Proc.Natl.Acad.Sci.USA, vol. 91, pp. 5252-5256 (1994).
Bicknell, R., "Vascular targeting and the inhibition of angiogenesis," Annals of Oncology, vol. 5, pp. 45-50 (1994)
Camussi, G. et al., "Angiogenesis induced in vivo by hepatocyte growth factor is mediated by platelet-activating factor stnthesis from macrophages," J. Immunol., vol. 158, pp. 1302-1309. (1997).
Flaumenhaft, R. et al., "Role od extracellular matrix in the action of basic fibroblast growth factor: Matrix as a source of growth factor for long-term stimulation of plasminogen activator production and DNA synthesis," Journal of Cellular Physiology, vol. 140, pp. 75-81 (1989).
Friesel, R.E. et al., "Molecular mechanisms of angiogenesis: fibroblast growth factor signal transduction," FASEB Journal, vol. 9, pp. 919-925 (1995).
Hunt, J.D. et al., "A Platelet-Activating Factor Antagonist, BN-50730, Inhibits Basic Fibroblast Growth Factor-Induced Human Umbilical Vein Endothelial Cell Proliferation and Tumor Xenograft Expansion in Athymic Nude Mice," submitted to Cancer, on Sep. 27, 2000.
Hunt, J.D. et al., "The Platelet-Activating Factor (PAF) Antagonist BN-50730 Inhibits Angiogenesis," Proceedings of the American Association for Cancer Research: Cell and Tumor Biology, vol. 41, abstract 4099 (2000).
Jaye, M. et al., "Human endothelial cell growth factor: cloning, nucleotide sequence, and chromosome localization," Science, vol. 233, pp. 541-546 (1986).
Lee. P.L. et al., "Purification and complementary DNA cloning of a receptor for basic fibroblast growth factor," Science, vol. 245, pp. 57-60 (1989).
Marchesell, V.L.L. and N.G. Bazan, "Platelet-activating factor is a messenger in the electroconvulsive shock-induced transcriptional activation of cfos and zif-268 in hippocampus," Journal of Neuroscience Research, vol. 37, pp. 54-61 (1994).
Marcheselli, V.L. et al., "Distinct platelet-activating factor binding sites in synaptic endings and intracellular membranes of rat cerebral cortex,"Journal of Biological Chemistry, vol. 265, pp. 9140-9145 (1990).
Montrucchio, G. et al., "Nitric oxide mediates angiogenesis induced in vivo by platelet-activating factor and tumor necrosis factor-α," American Journal of Pathology, vol. 151, pp. 557-563 (1997).
Montrucchio, G. et al., "Tumor necrosis factor α-induced angiogenesis depends on in situ platelet-activating factor biosynthesis," J. Exp. Med., vol. 180, pp. 377-382 (1994).
Pires, A.L.A. et al., "Long-lasting inhibitory activity of the hetrazepinic BN-50730 on exudation and cellualr alterations evokedby PAF and LPS," Br.J.Pharmacol., vol. 113, pp. 994-1000 (1994).
Silva, C.L. et al., "Formation of highly stable complex between BN-50730 [tetrahydro-4,7,8,10 methyl-1(chloro-2 phenyl)-6 (methoxy-4 phenyl-carbamoyl)-9 pyrido [4'3'-4, 5]thieno [3,2-f]triazolo-1,2,4 [4,3-a]diazepine-1,4]and the platelet-activating factor receptor in rabbit platelet membranes," Biochemical Pharmacology, vol. 51, pp. 193-196 (1996).

* cited by examiner

Primary Examiner—Dwayne Jones
(74) Attorney, Agent, or Firm—John H. Runnels; Bonnie J. Davis

(57) ABSTRACT

A novel use of platelet-activating factor antagonists that bind to intracellular PAF binding sites such as BN-50730 (tetrahedra-4,7,8,10 methyl-1 (chloro-1 phenyl)-6 (methoxy-4 phenyl-carbamoyl)-9 pyrido [4',3'-4,5] thieno [3,2-f] triazolo-1,2,4 [4,3-a] diazepine-1,4) has been discovered. These intracellular-binding platelet-activating factor antagonists were found to inhibit both in vivo and in vitro tumor growth and angiogenesis where the angiogenesis is stimulated by basic fibroblast growth factor.

7 Claims, 11 Drawing Sheets

[³H]DNA (mean CPM)

1 2 3 4 5 6

PLATELET-ACTIVATING FACTOR ANTAGONIST INHIBITION OF ANGIOGENESIS AND TUMOR GROWTH INDUCED BY BASIC FIBROBLAST

This invention pertains to a method to decrease tumor growth by inhibiting basic fibroblast growth factor ("bFGF")-stimulated tumor angiogenesis by treatment with a platelet-activating factor antagonist that binds to intracellular binding sites.

Angiogenesis, the development of new blood vessels, occurs in the normal body processes of development, wound healing, and reproduction. It is a complex process involving many stages, including extracellular matrix remodeling, endothelial cell migration and proliferation, capillary differentiation, and anastomosis. All detectable solid tumors exploit this normal process to supply the needed blood to proliferating tumor cells. Studies have demonstrated that the level of vascularization in a tumor is strongly associated with metastasis in melanoma, breast, and lung carcinomas. See R. Bicknell, "Vascular targeting and the inhibition of angiogenesis," Annals of Oncology, vol. 5, pp. 45–50 (1994).

A number of protein growth factors are known to induce angiogenesis, including vascular endothelial growth factor ("VEGF"), epidermal growth factor ("EGF"), insulin-like growth factor-1 ("IGF-1"), acidic fibroblast growth factor ("aFGF"), basic fibroblast growth factor ("bFGF"), tumor necrosis factor-2 ("TNF-2"), hepatocyte growth factor ("HGF"), and platelet-derived growth factor ("PDGF"). See R. E. Friesel et al., "Molecular mechanisms of angiogenesis: fibroblast growth factor signal transduction," FASEB Journal, vol. 9, pp. 919–925 (1995); M. Jaye et al., "Human endothelial cell growth factor: cloning, nucleotide sequence, and chromosome localization," Science, vol. 233, pp. 541–546 (1986); G. Camussi et al., "Angiogenesis induced in vivo by hepatocyte growth factor is mediated by platelet-activating factor synthesis from macrophages," J. Immunol., vol. 158, pp. 1302-1309 (1997); and L. Angelov et al., "Inhibition of angiogenesis by blocking activation of the vascular endothelial growth factor receptor 2 leads to decreased growth of neurogenic sarcomas," Cancer Research, vol. 59, pp. 5536–5541 (1999).

These peptide growth factors are known to stimulate angiogenesis using a wide range of differing cellular mechanisms. For example, WEB 2170, a platelet-activating factor ("PAF") antagonist, inhibited angiogenesis stimulated by both HGF and TNF-α, suggesting an intermediary role of PAF, but WEB 2170 did not inhibit angiogenesis stimulated by bFGF. See Camussi et al., 1997; and G. Montrucchio et al., "Nitric oxide mediates angiogenesis induced in vivo by platelet-activating factor and tumor necrosis factor-α," American Journal of Pathology, vol. 151, pp. 557–563 (1997).

The FGF family of growth factors regulates the proliferation and migration of capillary endothelial cells. The FGF family of growth factors currently includes nine members, of which aFGF and bFGF are considered prototypic. bFGF is produced by tumor cells, diffuses to capillary endothelial cells, and stimulates angiogenesis. See Friesel et al., 1995; and R. Flaumenhaft et al., "Role of extracellular matrix in the action of basic fibroblast growth factor: Matrix as a source of growth factor for long-term stimulation of plasminogen activator production and DNA synthesis," Journal of Cellular Physiology, vol. 140, pp. 75–81 (1989). bFGF is expressed in four forms: an 18-kDa form (155 amino acids), a 22-kDa form (196 amino acids), a 22.5-kDa form (201 amino acids), and a 24-kDa form (210 amino acids). The higher molecular weight forms of bFGF contain the complete 18-kDa amino acid sequence in addition to $NH_2$-terminal extensions of varying lengths. See P. L. Lee et al., "Purification and complementary DNA cloning of a receptor for basic fibroblast growth factor," Science, vol. 245, pp. 57–60 (1989).

Platelet-activating factor (PAF; 1-O-alkyl-2-acetyl-sn-glycero-3-phosphocholine) is a membrane-derived second messenger that is a potent mediator of inflammatory, ischemic, and immunological responses. PAF is rapidly produced in tissues in response to injury and other forms of stimulation. See N. G. Bazan et al., "Platelet-activating factor and retinoic acid synergistically activate the inducible prostaglandin synthase gene," Proc. Natl. Acad. Sci. USA, vol. 91, pp. 5252–5256 (1994). Intracellular and cell surface binding sites for PAF have been identified and distinguished by using diverse PAF antagonists that show a preference for one or more of the binding sites. See V. L. Marcheselli et al., "Distinct platelet-activating factor binding sites in synaptic endings and intracellular membranes of rat cerebral cortex," Journal of Biological Chemistry, vol. 265, pp. 9140–9145 (1990). Two binding sites found were associated with microsomal intracellular membranes and a third binding site was associated with the synaptosomal membrane (the extracellular plasma membrane). One of the internal microsomal binding sites displays the highest known affinity for PAF.

Several PAF antagonists have been identified. Most of the antagonists are competitive in nature. The antagonists can be divided into three distinct groups: PAF-related compounds such as CV 3988; synthetic PAF-unrelated compounds such as WEB 2086 and SR 27417; and natural products including BN-52021. See A. L. A. Pires et al., "Long-lasting inhibitory activity of the hetrazepinic BN-50730 on exudation and cellular alterations evoked by PAF and LPS," Br. J. Pharmacol., vol. 113, pp. 994–1000 (1994). A unique PAF antagonist, BN-50730, a hetrazepine, is known to displace PAF from microsomal membranes, but not from the synaptosomal, plasma membrane. See V. L. Marcheselli and N. G. Bazan, "Platelet-activating factor is a messenger in the electroconvulsive shock-induced transcriptional activation of c-fos and zif-268 in hippocampus," Journal of Neuroscience Research, vol. 37, pp. 54–61 (1994). Moreover, BN-50730 and WEB 2086, another PAF antagonist, are known to have different dissociation kinetics. See C. L. Silva et al., "Formation of a highly stable complex between BN-50730 [tetrahydro-4,7,8,10 methyl-1 (chloro-2 phenyl)-6 (methoxy-4 phenyl-carbamoyl)-9 pyrido [4',3'-4,5] thieno [3,2-f] triazolo-1,2,4 [4,3-α] diazepine-1,4] and the platelet-activating factor receptor in rabbit platelet membranes," Biochemical Pharmacology, vol. 51, pp. 193–196 (1996).

Angiogenesis stimulated by tumor necrosis factor (TNF-α) has been shown to be mediated, at least in part, by platelet-activating factor (PAF) synthesized from monocytes and endothelial cells. See G. Montrucchio et al., "Tumor necrosis factor α-induced angiogenesis depends on in situ platelet-activating factor biosynthesis," J. Exp. Med., vol. 180, pp. 377–382 (1994). TNF-α-induced angiogenesis was inhibited by WEB 2170, a specific PAF receptor antagonist that binds to the extracellular membrane. Additionally, angiogenesis stimulated by TNF-α was later shown to involve both nitric oxide and PAF. See G. Montrucchio et al., "Nitric oxide mediates angiogenesis induced in vivo by platelet-activating factor and tumor necrosis factor-α," American Journal of Pathology, vol. 151, pp. 557–563 (1997). This study also found that angiogenesis stimulated by bFGF was not inhibited by WEB 2170, leading the authors to conclude that bFGF-stimulated angiogenesis is PAF-independent.

In a later study, angiogenesis stimulated by hepatocyte growth factor (HGF) was found to be mediated by synthesis of PAF and inhibited by the specific PAF receptor antagonist WEB 2170. See G. Camussi et al., "Angiogenesis induced in vivo by hepatocyte growth factor is mediated by platelet-activating factor synthesis from macrophages," Journal of Immunology, vol. 158, pp. 1302–1309 (1997). These researchers also reported that angiogenesis induced by bFGF was not inhibited by WEB 2170.

We have surprisingly discovered that application of a PAF antagonist, such as "BN-50730" (also reported herein as "LAU-8080") (tetrahedra-4,7,8,10 methyl-1 (chloro-1 phenyl)-6 (methoxy-4 phenyl-carbamoyl)-9 pyrido [4',3'-4,5] thieno [3,2-f] triazolo-1,2,4 [4,3-α] diazepine-1,4), to both in vivo and in vitro tumor models of bFGF-stimulated angiogenesis causes a significant reduction in angiogenesis and tumor growth. We have discovered that the bFGF angiogenic pathway involves PAF. We found that the bFGF angiogenic pathway is inhibited by PAF antagonists that bind to intracellular PAF binding sites.

BRIEF DESCRIPTION OF DRAWINGS

FIG. 2b illustrates the treatment schedule of mice implanted with subcutaneous PC-3 xenografts used to generate the data in FIG. 2a.

FIG. 3b illustrates the treatment schedule of the mice implanted with orthotopic 201T xenografts used to generate the data in FIG. 3a.

FIG. 4b illustrates the treatment schedule of the mice implanted with subcutaneous PC-3 xenografts used to generate the data in FIG. 4a.

FIG. 10b illustrates the treatment schedule of the mice implanted with subcutaneous PC-3 xenografts used to generate the data in FIG. 10a.

Figure 1:
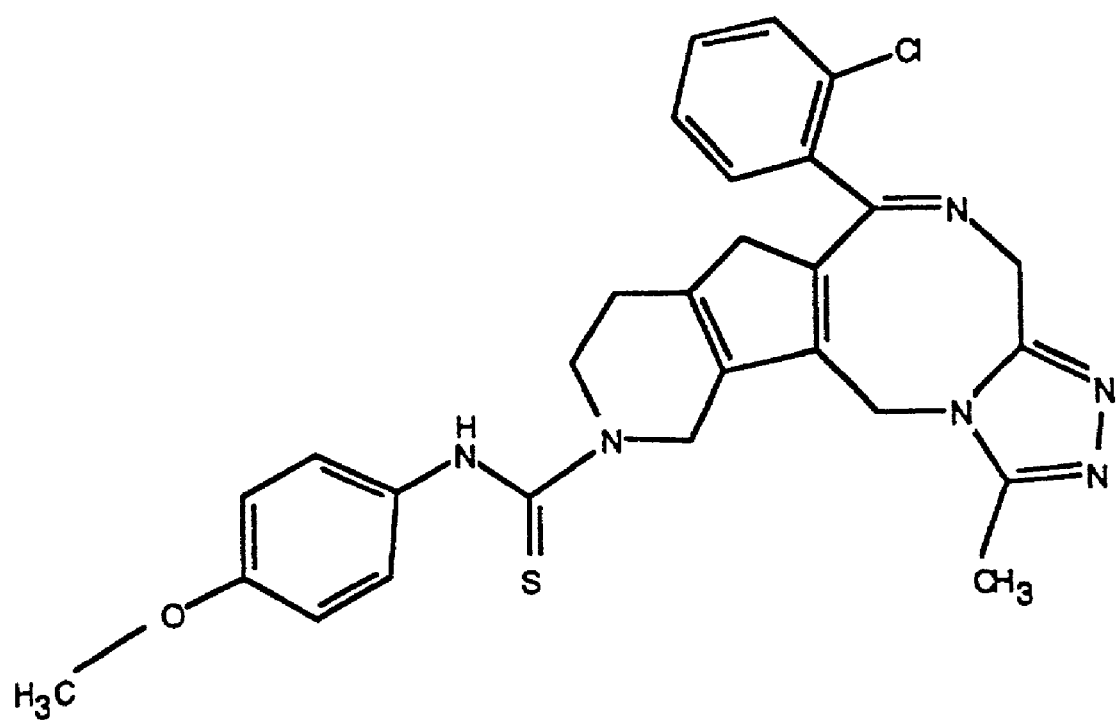
FIG. 1 illustrates the structure of BN-50730 (and "LAU-8080"), a PAF antagonist, that binds to intracellular PAF binding sites.

The present invention provides a new use for the PAF antagonist BN-50730 (or LAU-8080) and other PAF antagonists that bind to the intracellular PAF binding sites. LAU-8080 is the same compound as BN-50730, but is synthesized by a different mechanism. BN-50730 was surprisingly found to inhibit angiogenesis stimulated by bFGF, despite the literature reports that bFGF-stimulated angiogenesis was PAF-independent. Another PAF antagonist that is known to bind to the intracellular PAF binding sites is CV-3988. See V. L. Marcheselli et al., "Distinct platelet-activating factor binding sites in synaptic endings and in intracellular membranes of rat cerebral cortex," J. Biol. Chem., vol. 265, pp. 9140–9145 (1990).

As used herein, the term "bFGF-active PAF antagonist" refers to a PAF antagonist that binds to the intracellular PAF binding sites and inhibits angiogenesis otherwise stimulated by bFGF.

The bFGF-active PAF antagonist maybe administered to a patient by any suitable means, including parenteral, subcutaneous, intrapulmonary, and intranasal administration. Parenteral infusions include intramuscular, intravenous, intraarterial, or intraperitoneal administration. The bFGF-active PAF antagonist may also be administered transdermally, for example, in the form of a slow-release subcutaneous implant, or orally in the form of capsules, powders, or granules. It may also be administered by inhalation.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection maybe provided in the form of an ampule, each containing a unit dose amount, or in the form of a container containing multiple doses.

The bFGF-active PAF antagonist may be formulated into therapeutic compositions as pharmaceutically acceptable salts. These salts include the acid addition salts formed with inorganic acids such as, for example, hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery may be achieved by admixing the active ingredient with appropriate macromolecules, for example, polyesters, polyamino acids, polyvinyl pyrrolidone, ethylenevinylacetate, methylcellulose, carboxymethylcellulose, prolamine sulfate, or lactide/glycolide copolymers. The rate of release of the bFGF-active PAF antagonist may be controlled by altering the concentration of the macromolecule.

Another method for controlling the duration of action comprises incorporating the bFGF-active PAF antagonist into particles of a polymeric substance such as a polyester, peptide, hydrogel, polylactide/glycolide copolymer, or ethylenevinylacetate copolymers. Alternatively, the bFGF-active PAF antagonist maybe encapsulated in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

The term "therapeutically effective amount" as used herein refers to an amount of the bFGF-active PAF antagonist sufficient to decrease angiogenesis and tumor cell proliferation. The term "therapeutically effective amount" therefore includes, for example, an amount of an bFGF-active PAF antagonist sufficient to prevent the growth of the patient's tumor, and preferably to reduce by at least 50%, and more preferably to reduce by at least 90%, the mass of a patient's tumor. The dosage ranges for the administration of the bFGF-active PAF antagonist are those that produce the desired effect. Generally, the dosage will vary with the age, weight, condition, sex of the patient, type of tumor, and degree of tumor development. A person of ordinary skill in the art, given the teachings of the present specification, may readily determine suitable dosage ranges. The dosage can be adjusted by the individual physician in the event of any contraindications. In any event, the effectiveness of treatment can be determined by monitoring the extent of tumor growth and remission by methods well known to those in the field.

EXAMPLE 1

Materials and Methods

BN-50730 or LAU-8080

The structure of the PAF antagonist, tetrahydro-4,7,8,10 methyl-1 (chloro-2 phenyl)-6 (methoxy-4 phenyl-carbomoyl)-9 pyrido [4',3'-4,5] thieno [3,2-f] triazolo-1,2,4[4,3-α] diazepine-1,4 is shown in FIG. 1. This compound, known as BN-50730, was initially obtained from Beaufoure-Ipsen, France. The term "LAU-8080" is used in the examples to refer to a compound obtained from the Universidad de Alcala, Madrid, Spain, with the same structure as BN-50730, but synthesized by a different method than the compound from Beaufoure-Ipsen. See International Application No. WO 01/83440. Thus, in the following examples, the designation of the compound as "BN-50730" or "LAU-8080" is used to identify the source of the compound. In the rest of the specification and claims, the name "BN-50730" is used as the generic name for the PAF antagonist shown in FIG. 1.

The compound was dissolved in DMSO (dimethyl sulfoxide) and stored at −20° C. as a 5.5 mM stock solution.

Cell Lines and Growth Conditions

The human prostatic carcinoma cell line PC-3 was grown in RPMI 1640 (Life Technologies, Grand Island, Nebr.) supplemented with 10% fetal bovine serum ("FBS", Life Technologies). The human cell line 201T was established from a poorly differentiated lung adenocarcinoma, as previously described using the method of J. M. Siegfried et al., "Secretion of autocrine growth factors by cultured lung tumors: effects on neoplastic lung epithelial cells," Lung Cancer, vol. 4, pp. 205–209 (1988). See also J. P. Hamide et al., "Percutaneous implantation of non-small cell lung carcinoma: technique and observations," Academ. Radiolo., vol. 4, pp. 629–633 (1997). The cell line was grown in a medium conditioned for 48 hours by the cell line A549 (ATCC CCL-185) containing 1% FBS (HyClone Laboratories, Logan, Utah) as previously described in J. M. Siegfried, "Culture of primary lung tumors using medium conditioned by a lung carcinoma cell line," J. Cell. Biochem., vol. 41, pp. 91–95 (1988). This medium is referred to as CM+1% FBS.

Human umbilical vein endothelial cells ("HUVEC") were propagated in one of three growth media depending on the experimental conditions. HUVEC were maintained in endothelial basal medium ("EBM-2") (Clonetics, Walkersville, Md.) supplemented with 2% FBS (Clonetics). HUVEC were also grown in endothelial growth medium ("EGM") (Clonetics), which contained 3 mg/ml (protein content) bovine brain extract, 10 ng/ml EGF (endothelial growth factor), 1 μg/ml hydrocortisone, 2% FBS, gentamicin, and amphotericin-B. HUVEC were likewise grown in EGM-2, supplemented with VEGF (vascular epithelial growth factor), $R^3$-IGF-1 (long recombinant-3 insulin-like growth factor-1), ascorbic acid, heparin, 2% FBS, EGF, bFGF, gentamicin, and amphotericin-B.

All cell lines were grown in a humidifed incubator in 5% $CO_2$ at 37° C. Cell monolayers approaching 75% confluency were harvested using the De Larco formulation of trypsin-EDTA (Life Technologies) and were subcultured for serial passage.

Experimental Animals

Pathogen-free 4 to 6 week-old male NCr athymic nude mice (Taconic, Germantown, N.Y.) were housed in sterilized, filter-topped cages kept in laminar flow isolators (Forma Scientific, Marietta, Ohio), and fed autoclaved food and water ad libitum. Four animals were housed in each cage. Mice were acclimated to the vivarium for one week prior to their use in study protocols. All procedures involving the mice were performed under sterile conditions in a laminar flow hood (Forma Scientific). All studies were approved by the institutional animal care and use committee.

Tumor Implantation and Growth

Human PC-3 prostate cancer cells ($2 \times 10^6$ cells; American Type Culture Collection CRL-1435) were inoculated subcutaneously into the flanks of nude mice in 0.1 ml HBSS (Hank's balanced salt solution) (Life Technologies). For implantation of orthotopic 201T cells, animals were fully anesthetized in a Harvard small animal anesthesia chamber using nebulized Metafane (Pitman Moore, Inc., Washington Crossing, N.J.). Intrathoracid injections were performed at the lateral dorsal midaxillary line just inferior to the scapular angle using a 1.2 cm, 27-gauge needle. The needle was advanced through the chest wall into the lung tissue, and the tumor cell inoculum of $2 \times 10^6$ cells was then dispersed in a final volume of 0.1 ml HBSS/Matrigel (1:1 ratio). Animals were allowed to recover from anesthesia for approximately 10 min under heat lamps to maintain body temperature. The orthotopic implantation technique is further described in Hamide et al., 1997. For tumors implanted subcutaneously, tumors were measured in a blind fashion with dial calipers, and the volume was calculated using the formula $\frac{1}{2} \ast \pi (W \ast L \ast H)$. For orthotopically implanted 201T cells, tumors were detected in these mice by weighing the excised mediastinal block (heart, lung, and tumor if present) and comparing these weights to the mediastinal blocks from litter mates who did not receive tumor implantation.

In vitro Cell Growth Assays

PC-3 cells were exposed to 0, 0.1, 1, 2.5, 5, and 10 $\mu$M BN-50730 in RPMI medium supplemented with 10% FBS and [$^3$H]thymidine (Amersham Life Science, Arlington Heights, Ill.). 201T cells were exposed to 0, 0.1, 1, 2.5, 5, and 10 $\mu$M BN-50730 in CM+1% FBS supplemented with [$^3$H]thymidine. The cells were allowed to propagate for 5 days in the presence of BN-50730 or DMSO, followed by the measurement of acid-perceptible [$^3$H]DNA by liquid scintillation counting. PC-3 and 201T cells were also exposed to 10 $\mu$M BN-50730 for 24, 48, 72 and 144 hours, and cell growth assessed as above.

Western Blot Analysis

HUVEC, PC-3, and 201T cells were grown to 75% confluency in the appropriate growth media. BN-50730 (5 $\mu$M) or vehicle (DMSO) was added to each cell line 18 hr prior to cell harvest. Cells were washed three times in phosphate-buffered saline ("PBS") and scraped into Lemely buffer which lacked bromophenol blue and $\beta$-mercaptoethanol (0.1 M NaCl, 0.01M Tris-HCl (pH 7.6), 0.001 M EDTA, 1 $\mu$g/ml aprotinin, 100 $\mu$g/ml phenylmethylsulfonyl flouride, 2% SDS, and 10% glycerol). The cell suspension was boiled for 10 min and then immediately stored at $-20°$ C. Protein levels were quantified using a Bio-Rad Protein Assay (Bio-Rad, Hercules, Calif.). Protein samples (20 $\mu$g) were separated through a 10–20% denaturing gradient acrylamide gel in Tris-glycine buffer and transferred to nitrocellulose (Bio-Rad) by electrophoretic blotting. The nitrocellulose was blocked in 0.4% non-fat dry milk and incubated for 1 hr at 4° C. with mouse anti-human bFGF monoclonal IgG$_1$ antibody (3H3, Oncogene Research Products, Cambridge, Mass.). Primary antibody was detected using alkaline phosphatase-conjugated goat anti-mouse IgG (Bio-Rad).

Statistics

Statistical analyses were done on a Macintosh PowerPC G3 using Statview 4.51 (Abacus Concepts, Inc., Berkeley, Calif.). Significance was set at $p<0.05$.

EXAMPLE 2

Inhibition of Tumor Formation by BN-50703 or LAU-8080

Figure 2A:
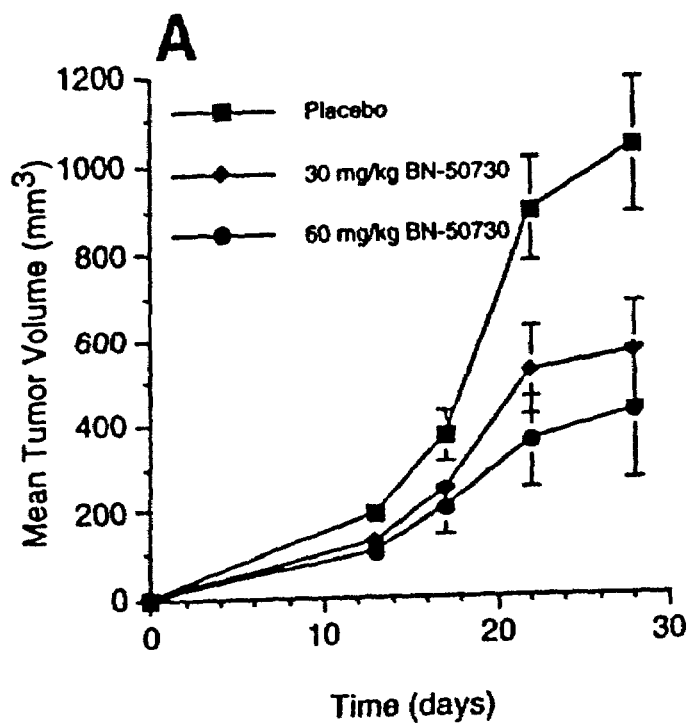
FIG. 2a illustrates the temporal change of tumor volume in mice implanted with subcutaneous PC-3 xenografts under three experimental conditions, including multiple treatments with 30 mg/kg BN-50730 or with 60 mg/kg BN-50730.
Figure 2B:
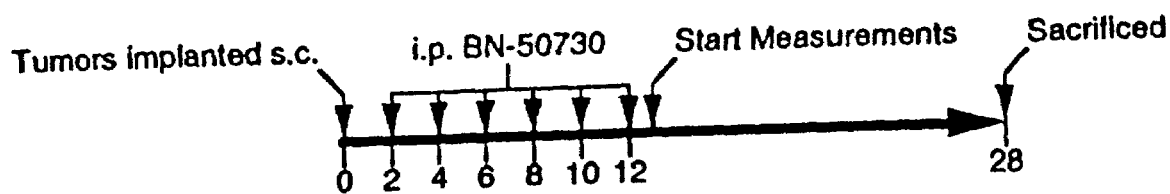

Potential anti-angiogenic and anti-tumor effects of the PAF antagonist BN-50730 were tested on human tumor xenografts in the NCr athymic nude mice. Thirty mice were implanted with subcutaneous human prostatic carcinoma cells, PC-3, at day 0, and were randomized into three groups. Mice were treated either with a placebo, 30 mg/kg BN-50730, or 60 mg/kg BN-50730 at days 2, 4, 6, 8, 10, and 12 as shown in the schedule of FIG. 2b. Animals were sacrificed at day 13, 17, 21 and 28, and the volumes of the subcutaneous tumors were measured using dial calipers and the formula $\frac{1}{2} \ast \pi (W \ast L \ast H)$ as described in Example 1. A significant dose-dependent reduction in tumor size was seen ($p<0.001$) (FIG. 2a).

Figure 3A:
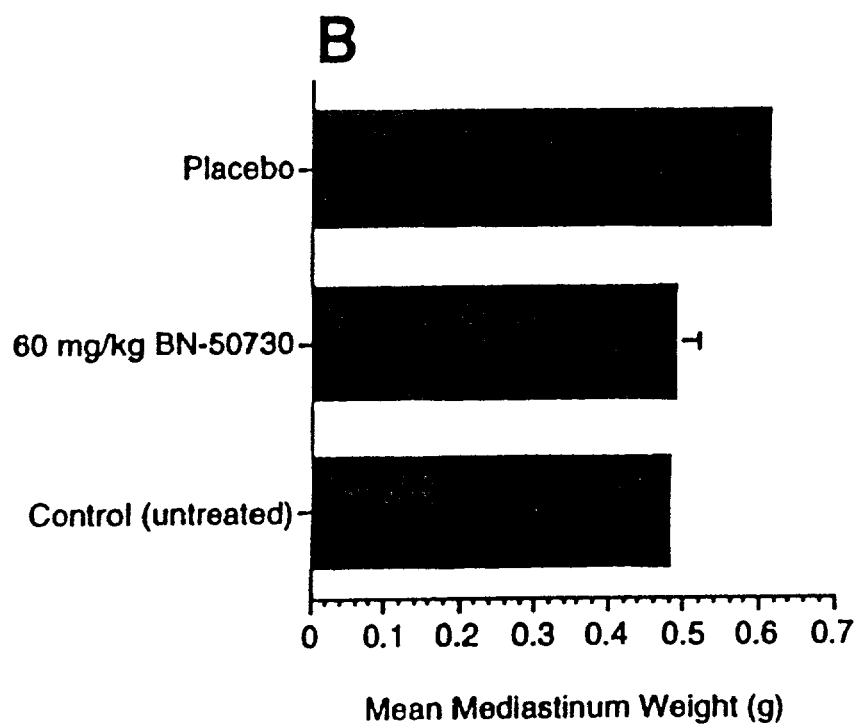
FIG. 3a illustrates the differences in tumor weight in mice implanted with orthotopic 201T xenografts under three experimental conditions, including an untreated control, treatment with a placebo, and treatment with 60 mg/kg LAU-8080.
Figure 3B:
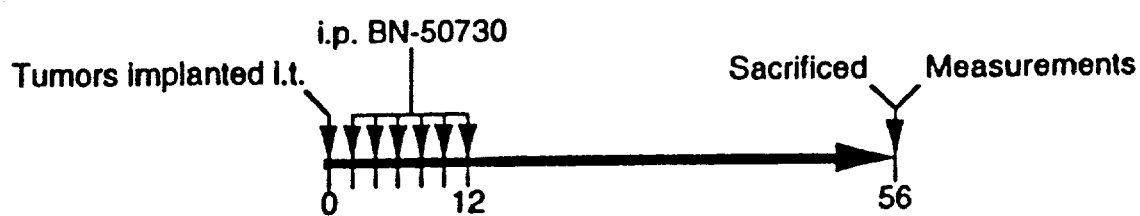

Another set of mice was randomized into three groups. Two groups were implanted orthotopically with human 201T lung adenocarcinoma cells at day 0. The control, unimplanted group received no treatment. The two implanted groups were treated either with a placebo or with 60 mg/kg LAU-8080. The treatments were given at days 2, 4, 6, 8, 10, and 12 as shown in FIG. 3b; and the animals were sacrificed at day 56. (FIG. 3b). The mediastinal blocks containing the heart, lungs, and tumors (if present) were excised upon necropsy and weighed. The mediastinal blocks were significantly larger in placebo-treated animals as compared to those treated with LAU-8080 ($p=0.011$, Student's t-test). (FIG. 3a). As seen in FIG. 3a, the mediastinal weight of LAU-8080-treated animals was the same as for control liter mates who did not receive tumor cell implantation or drug treatment ($p=0.800$, Student's t-test).

Figure 4A:
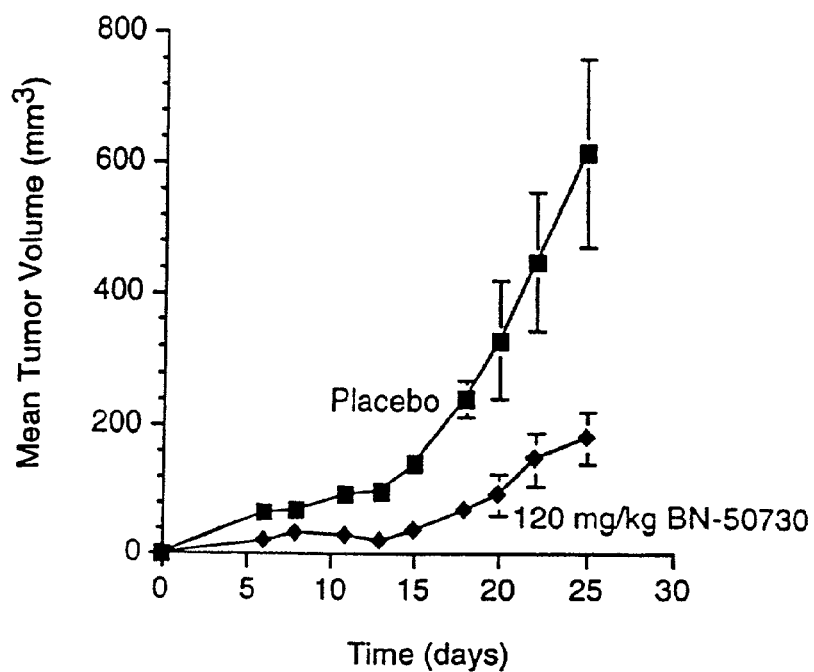
FIG. 4a illustrates the temporal change in tumor volume in mice implanted with subcutaneous PC-3 xenografts after multiple treatments with 120 mg/kg LAU-8080.
Figure 4B:
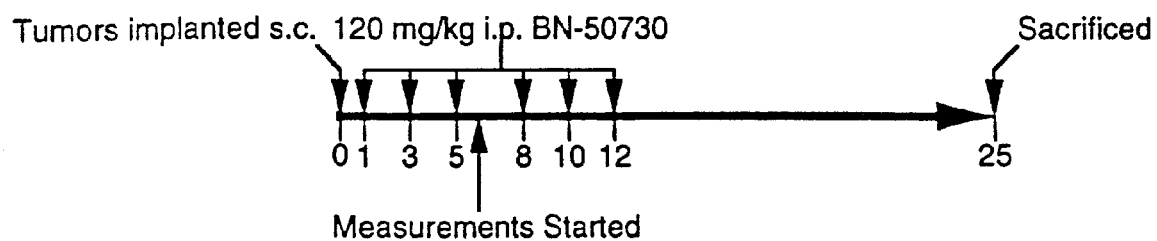

In a separate experiment to determine the effects of a high dose of LAU-8080 dissolved in 2-hydroxypropyl-$\beta$-cyclodextran (instead of DMSO) on PC-3 xenografts, mice were treated as shown in FIG. 4b. Tumors were implanted subcutaneously at day 0. The mice were then divided into two groups to receive injections of either a placebo or 120 mg/kg LAU-8080 on days 1, 3, 5, 8, 10, and 12. Mice were sacrificed on days 6, 8, 11, 13, 15, 18, 20, 21, and 25; and the volumes of the tumors were measured as described above. The mice treated with the high dose of LAU-8080 had significantly smaller tumors as compared to the placebo-treated mice ($p=0.0001$, F-test). (FIG. 4a). The tumors in the mice treated with LAU-8080 did not begin to increase in size until after treatment was stopped at day 12.

BN-50730 (or LAU-8080) significantly reduced the size of subcutaneous and intrathoracic tumors in nude mice. Based on visual observations, there were no apparent side effects in mice treated at any dose of BN-50730.

Nude mice could be used to test the effects of BN-50730 on other known tumor cells in a procedure similar to that discussed above in Examples 1 and 2. The nude mice would be implanted with commercially available tumor cells and then treated with BN-50730 to determine its effect on tumor size.

EXAMPLE 3

BN-50730 Had Minimal Effect on Tumor Proliferation in vitro.

Figure 5A:
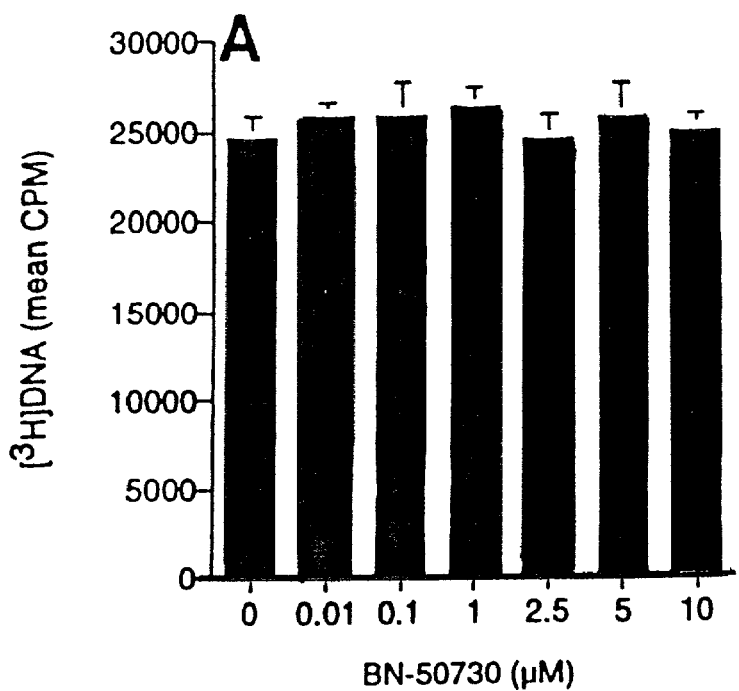
FIG. 5a illustrates the effect of various concentrations of BN-50730 on in vitro cell proliferation of PC-3 cells as measured by [$^3$H]thymidine incorporation.
Figure 5B:
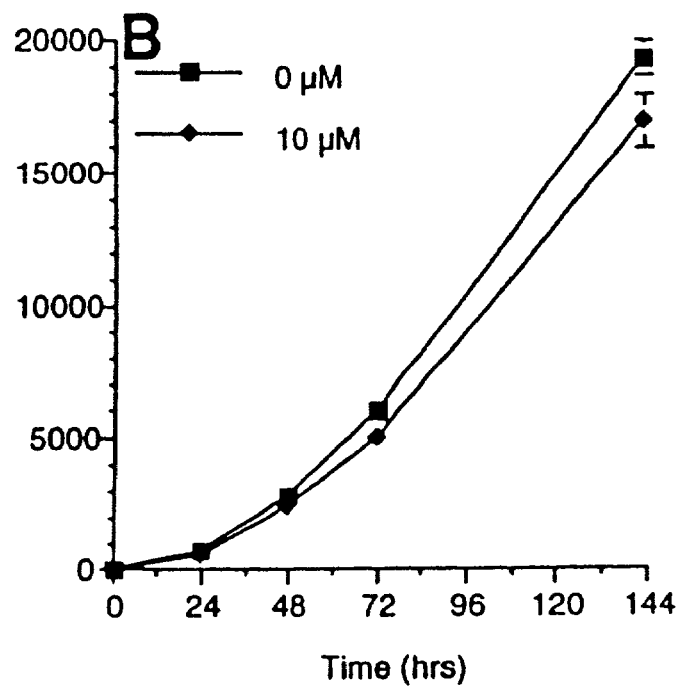
FIG. 5b illustrates the effect of 10 µM BN-50730 on in vitro cell proliferation over time of PC-3 cells as measured by [$^3$H]thymidine incorporation.

To determine whether if BN-50730 affected the growth of tumor cells in vitro, concentration response and time course experiments were performed on the prostatic carcinoma cell line PC-3 and on the lung adenocarcinoma cell line 201T using [$^3$H]thymidine incorporation assays. As seen in FIG. 5a, PC-3 cells were not affected by treatment with BN-50730 when treated for 4 days with concentrations of 0.01, 0.1, 1, 2.5, 5, and 10 µM BN-50730 (p=0.529 for 10 µM, Student's t-test). There was no effect from treatment with 10 µM BN-50730 at 1, 2, 3, or 6 days (FIG. 5b; p=0.556, F-test). This indicated that the in vivo decrease in tumor growth was due to an antiangiogenic effect.

Figure 5C:
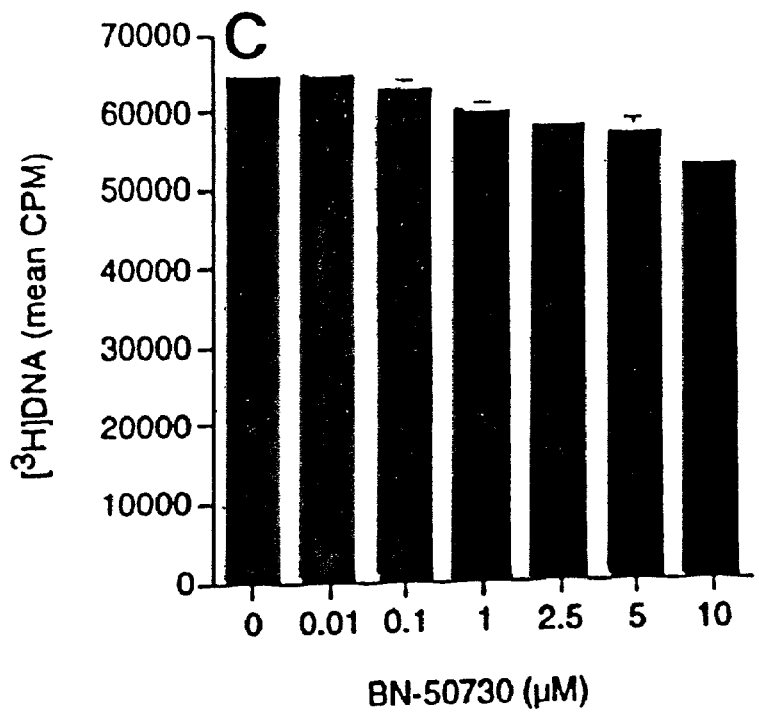
FIG. 5c illustrates the effect of various concentrations of BN-50730 on in vitro cell proliferation of 201T cells as measured by [$^3$H]thymidine incorporation.
Figure 5D:
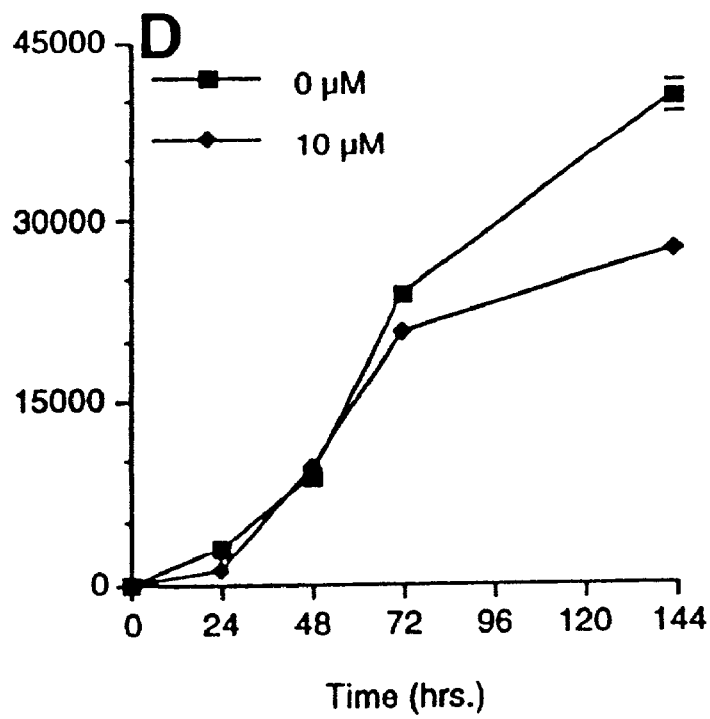
FIG. 5d illustrates the effect of 10 µM BN-50730 on in vitro cell proliferation over time of 201T cells as measured by [$^3$H]thymidine incorporation.

However, a concentration-dependent reduction in growth of 201T cells was observed when treated with the above concentrations of BN-50730 for four days (FIG. 5c, p<0.005 for concentrations at or above 1.0 µM, Student's t-test). The six-day time course for 201T cells exposed to 10 µM BN-50730 demonstrated that the growth inhibition was manifested after 72 hr of exposure. Although the inhibition in growth was large after 144 hr of exposure, the curves were not statistically different (FIG. 5d, p=0.081, F-test). This result, seemingly contradictory, was explained by the results presented below in Example 5.

EXAMPLE 4

BN-50730 Inhibits Growth of HUVEC in vitro.

Figure 6:
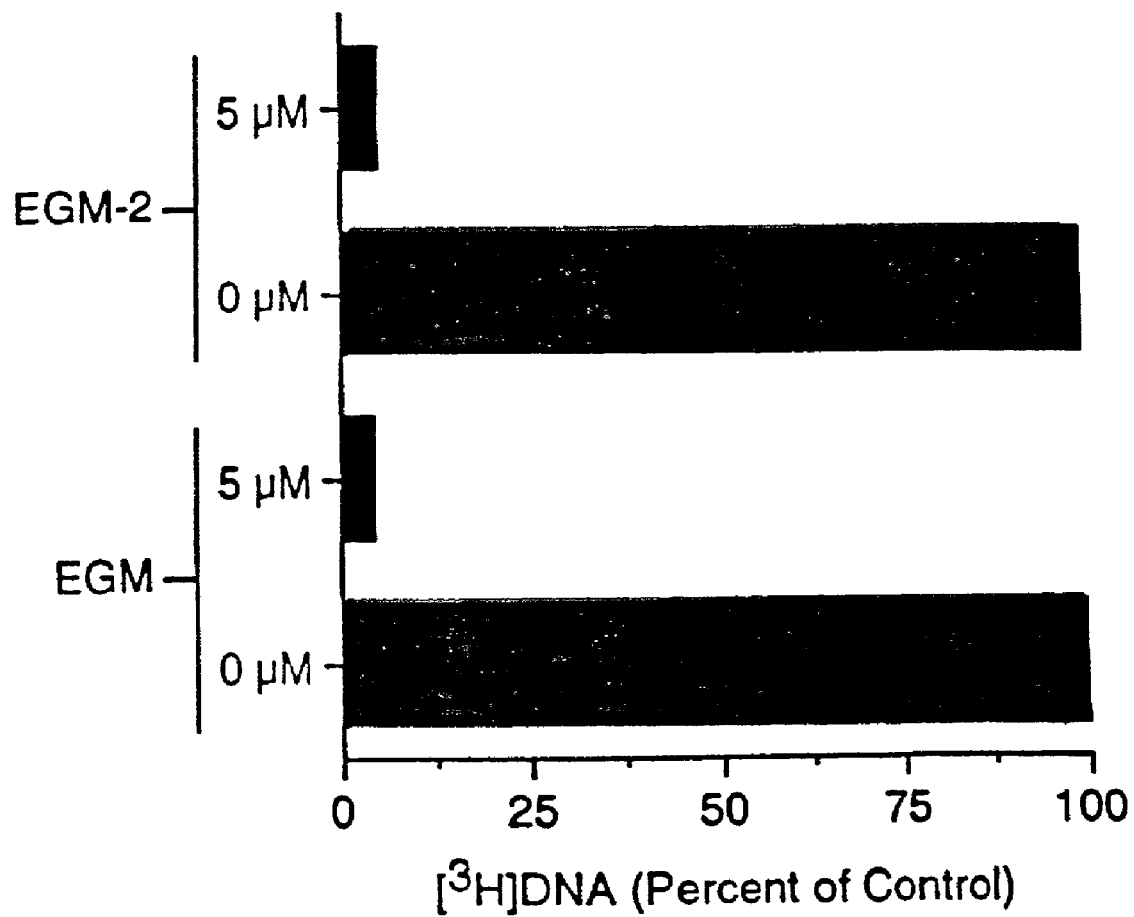
FIG. 6 illustrates the inhibitory effect of 5 µM BN-50730 on in vitro cell proliferation as measured by [$^3$H]thymidine incorporation of human umbilical vein endothelial cells grown in EGM-2 and EGM growth-factor enhanced media.

Based on the above in vitro tumor data, the effect of BN-50730 on tumor growth is believed to result from inhibition of angiogenesis. To test this theory, the effect of BN-50730 on angiogenesis of HUVEC cells was measured using two growth media designed to induce rapid proliferation, EGM or EGM-2. HUVEC growth was measured by [$^3$H]thymidine incorporation into DNA. Under both growth conditions, 5 µM BN-50730 significantly reduced the growth of HUVEC (FIG. 6, p=0.001, Student's t-test).

EXAMPLE 5

BN-50730 Inhibits HUVEC Proliferation Stimulated by Tumor-Conditioned Media.

Figure 7:
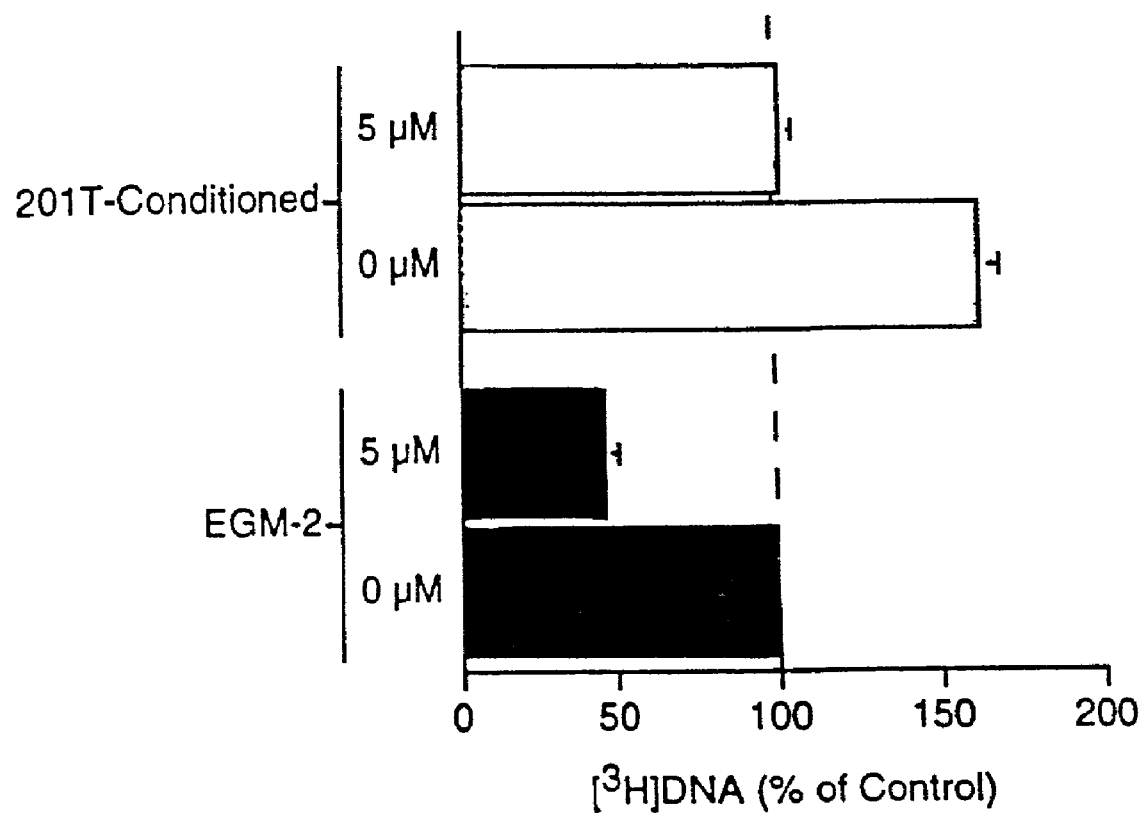
FIG. 7 illustrates the inhibitory effect of 5 µM BN-50730 on in vitro cell proliferation as measured by [$^3$H]thymidine incorporation of human umbilical vein endothelial cells in either 201T-conditioned medium or EGM-2 growth-factor enhanced growth medium.

As many tumors are known to produce angiogenesis-inducing factors, an experiment was conducted to test for increased proliferation of HUVEC cells exposed to 201T-conditioned medium. 201T cells were allowed to condition basal medium (EBM supplemented with 2% FBS) for 48 hr. This medium does not contain any additional growth factors other than those present in the FBS. As seen in FIG. 7, greater stimulation of HUVEC growth was associated with exposure to medium conditioned by 201T cells as compared to fresh EGM-2 medium. EGM-2 is a medium containing the growth factors bFGF, VEGF, IGF-1, and EGF. As shown in FIG. 7, the stimulation of HUVEC growth in either medium was inhibited by the addition of 5 µM BN-50730.

Based on these results, it is clear that the tumor cell line 201T produces soluble growth factors that induce rapid proliferation of HUVEC, and that the effect of this stimulation can be inhibited by BN-50730, a PAF antagonist that binds to intracellular PAF binding sites. This also explains the inhibition of 201T cells seen in Example 3.

EXAMPLE 6

BN-7030 blocks bFGF-induced Proliferation of HUVEC Cells.

Figure 8A:
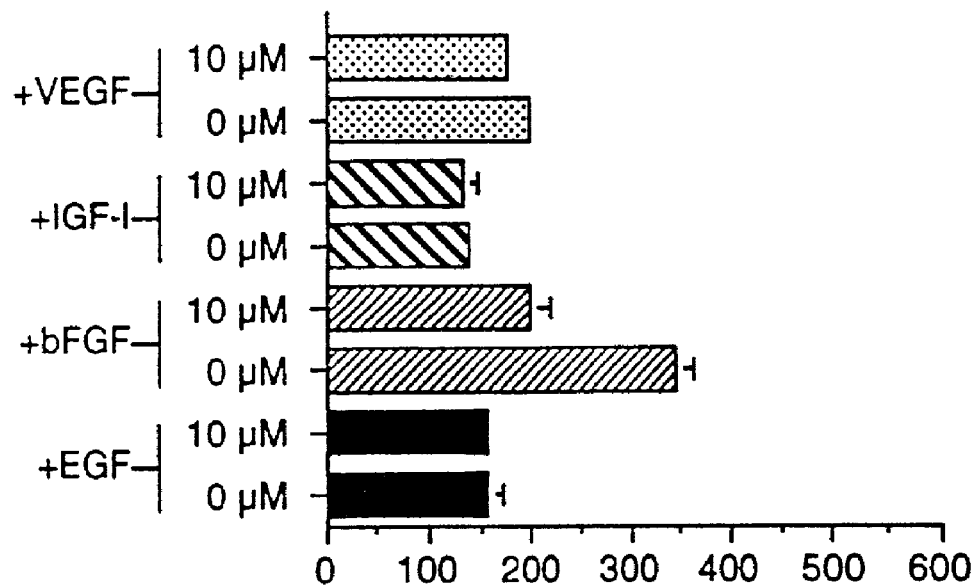
FIG. 8a illustrates the effect of 10 µM BN-50730 on in vitro cell proliferation as measured by [$^3$H]thymidine incorporation of human umbilical vein endothelial cells in medium enhanced by a single growth factor.

To characterize the inhibitory effects of BN-50730 on HUVEC proliferation, a series of growth assays was performed in which growth factors were either added or omitted singly from the growth medium in the presence or absence of BN-50730. The cells were grown in a medium supplemented with [$^3$H]thymidine, in either the presence or absence of BN-50730. Cells that proliferate will incorporate [$^3$H]thymidine into their DNA. In the first experiment, individual growth factors VEGF, IGF-1, bFGF, or EGF were added to EBM-2 supplemented with 2% FBS. As seen in FIG. 8a, the inhibitory effect of BN-50730 depended on which growth factor was used. A small, but significant (p=0.036, Student's t-test) reduction in HUVEC growth was observed when 10 µM BN-50730 was included in the medium containing VEGF. No difference was seen in the media with either IGF-1 or EGF. However, a larger reduction was observed in the medium containing bFGF (p=0.0002). This experiment supports the hypothesis that different cellular mechanisms use different peptide growth factors.

Figure 8B:
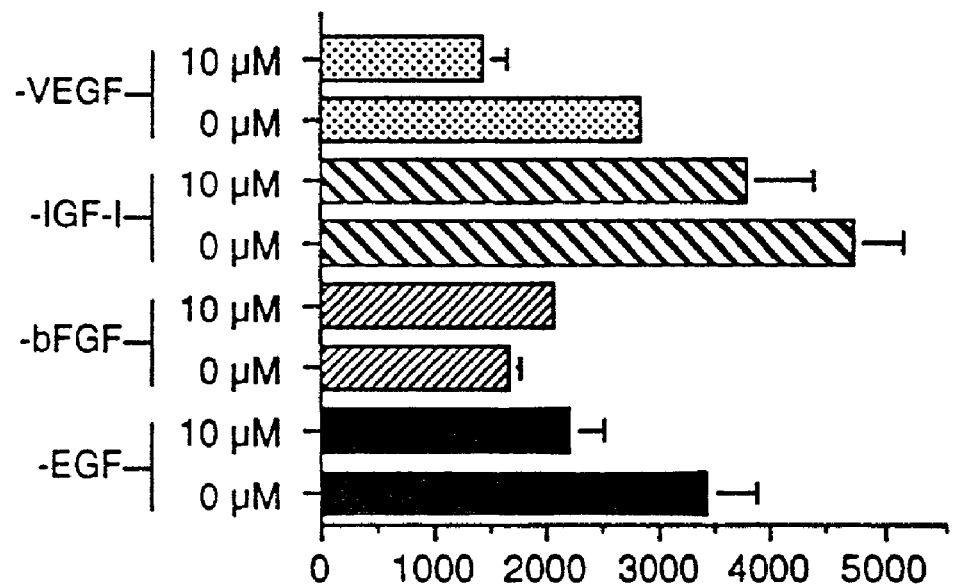
FIG. 8b illustrates the effect of 10 µM BN-50730 on in vitro cell proliferation as measured by [$^3$H]thymidine incorporation of human umbilical vein endothelial cells in growth-factor enhanced media that is missing a single growth factor.

In a subsequent experiment, mixtures of the growth factors were analyzed, with only one growth factor absent from the medium, and each of the other three were present, in the presence or absence of 10 µM BN-50730. As shown in FIG. 8b, a reduction in growth was observed when the medium lacked only VEGF, IGF-1 or EGF. However, no reduction was seen when bFGF was absent.

These results show that BN-50730 reduces the growth of HUVEC stimulated by bFGF. BN-50730 inhibited the bFGF pathway that would otherwise stimulate angiogenesis. The data also show that the growth factors VEGF, IGF-1, and EGF do not stimulate angiogenesis using the same PAF pathway as bFGF. Because BN-50730 is a known PAF antagonist that binds to intracellular binding sites, it is now believed that bFGF stimulates angiogenesis using an intracellular PAF-mediated mechanism.

EXAMPLE 7

201T and PC-3 Cell Lines Produce bFGF.

Figure 9:
FIG. 9 illustrates the results of a Western blot analysis of cell lysates for bFGF of human umbilical vein endothelial cells (lanes 1 and 2), PC-3 cells (lanes 3 and 4), or 201T cells (lanes 5 and 6) grown in the presence (lanes 2, 4, and 6) or absence (lanes 1, 3, and 5) of BN-50730.

To demonstrate that 201T and PC-3 cell lines both produce bFGF, a western blot analysis was performed on cell lysates for the presence of bFGF. The methods were as in Example 1. The results are shown in FIG. 9. Lysates were analyzed from HUVEC cells grown in the presence of DMSO (Lane 1) or 5 µM BN-50730 (Lane 2); PC-3 cells grown in the presence of DMSO (Lane 3) or 5 µM BN-50730 (Lane 4); and 201T cells grown in the presence of DMSO (Lane 5) or 5 µM BN-50730 (Lane 6). Not surprisingly, HUVEC did not produce bFGF. However, both 201T and PC-3 cells produced bFGF in both the presence and absence of BN-50730. This demonstrates that BN-50730 does not inhibit the production of bFGF, but acts through another mechanism.

EXAMPLE 8

Comparison of Anti-Tumor Effect of BN-50730 with that of IFN-2α

Infantile cutaneous hemangiomas are capillary bed tumors that demonstrate rapid growth during the first year of life. They have been shown to express high levels of the angiogenic factors bFGF and VEGF and low levels of the negative regulatory factor interferon β(IFN-β). See D. R. Bielenberg et al., "Progressive growth of infantile cutaneous hemangiomas is directly correlated with hyperplasia and angiogneesis of adjacent epidermis and inversely correlated with expression of the endogenous angiogenesis inhibitor, IFN-β," Int. J. Cancer, vol. 14, pp. 401–408 (1999). IFN-β inhibits endothelial cell migration; and when injected around tumors, it damages blood vessels, leading to necrosis. Several types of tumors have been successfully treated with IFN-2α. See E. Chang et al., "Successful treatment of infantile hemangiomas with interferon-alpha-2β," J. Pediatric Hematol. Oncol., vol. 19, pp. 237–244 (1997); R. A. Ezekowitz et al., "Interferon alpha-2α therapy for life-threatening hemangiomas of infancy," N. Engl. J. Med., vol. 326, pp. 1456–1463 (1992); and C. W. White et al., "A treatment of childhood angiomatous disease with recombinant interferon alpha-2α," J. Pediatr., vol. 188, pp. 59–66 (1991).

Figure 10A:
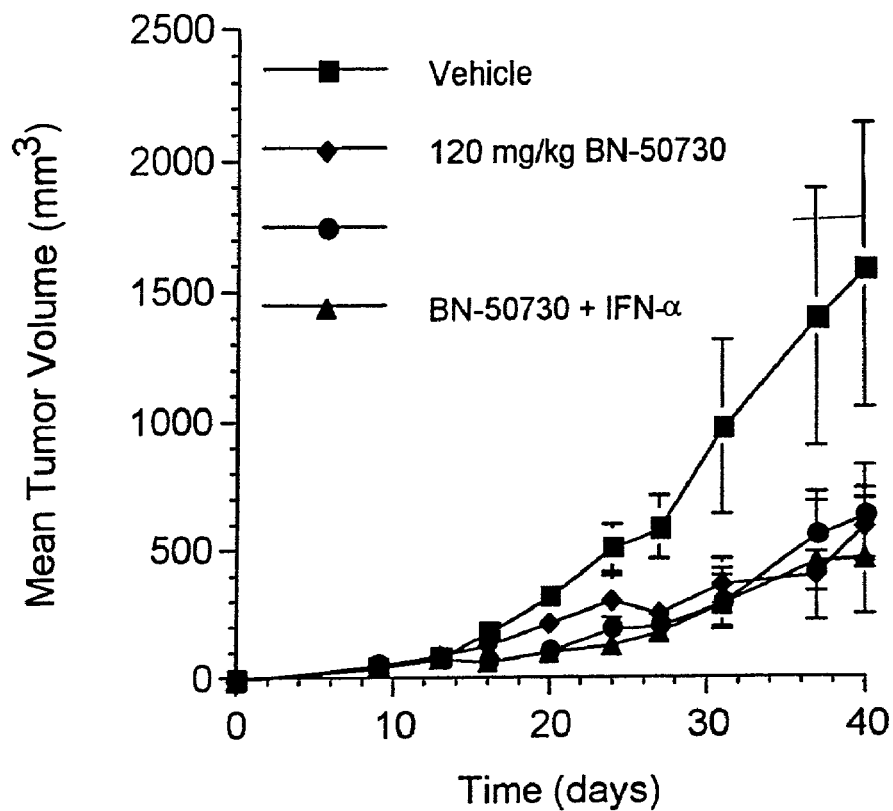
FIG. 10a illustrates the temporal change in tumor volume in mice implanted with subcutaneous PC-3 xenografts treated with a placebo, with 120 mg/kg LAU-8080, with a 1000 units of IFN-α, and with both LAU-8080 and IFN-α.
Figure 10B:
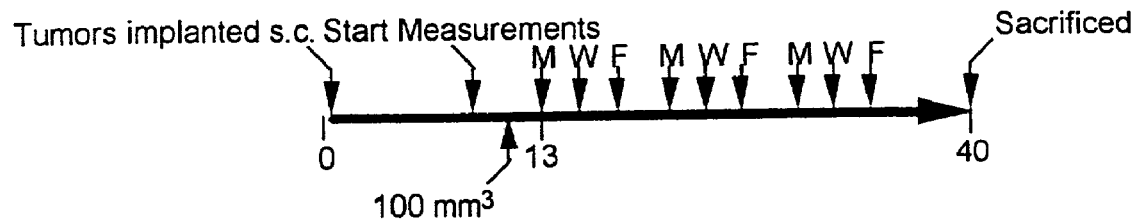

To compare the potential anti-tumor effect of BN-50730 with the FDA human-approved antiangiogenic compound IFN-2α, nude mice bearing PC-3 xenografts were treated with either 120 mg/kg BN-50730 (n=6), 1,000 U human IFN-2a (n=6) (Sigma Chemical Co., St. Louis, Mo.), 120 mg/kg BN-50730+1,000 U human IFN-2a (n=6), or with vehicle alone (Control, n=6). Tumors were implanted at day 0. The tumors were allowed to expand to 100 mm³ before treatment was initiated as shown in the schedule in FIG. 10b. Tumor measurements were begun on day 9. Treatments of the different groups were on days 13, 15, 17, 20, 22, 24, 27, 29, and 31. Tumor measurements were taken on days 13, 16, 20, 24, 27, 31, 37, and 40. As seen in FIG. 10a, each of the treatment groups resulted in significantly smaller tumors as compared to control animals (p<0.001, F-test). There was no significant difference in the size of tumors in BN-50730-treated mice versus IFN-2a-treated mice (p=0.089, F-test). Therefore, based on these limited preliminary data, BN-50730 appears to have an effectiveness as comparable to that of IFN-2α on established PC-3 xenografts in nude mice.

The use of downstream inhibitors of angiogenesis as therapeutic options is an intriguing possibility. Many inhibitors of growth factors or their receptors have been tested for their potential as anti-angiogenesis therapeutic agents. These compounds typically target only one specific growth factor cascade and may lack the broad applicability that second messenger inhibitors, like BN-50730, may possess. Therefore, the combination of BN-50730 with other known anti-angiogenic compounds may dramatically increase the efficacy of those agents. Examples of other known antiangiogenic compounds that might prove effective in combination with BN-50730 include WEB 2086, INF-2α, TNP-470, endostatin, SU 5416, SU 6668, batimistat, angiostatin and celecoxib. See D. Inger et al., "Synthetic analogues of fumagillin that inhibit angiogenesis and suppress tumour growth," Nature, vol. 348, pp. 555–7 (1990); M. S. O'Reilly et al., "Endostatin: an endogenous inhibitor of angiogenesis and tumor growth," Cell, vol. 88, pp. 277–85 (1997); T. A. Fong et al., "SU5416 is a potent and selective inhibitor of the vascular endothelial growth factor receptor (Flk-1/KDR) that inhibits tyrosine kinase catalysis, tumor vascularization, and growth of multiple tumor types," Cancer Res., vol. 59, pp. 99–106 (1999); A. D. Laird et al., "SU6668 is a potent antiangiogenic and antitumor agent that induces regression of established tumors," Cancer Res., vol. 60, pp. 4152–60 (2000); R. D. Kenagy et al., "The role of plasminogen, plasminogen activators, and matrix metalloproteinases in primate arterial smooth muscle cell migration," Arterioscler. Thromb. Vasc. Biol., vol. 16, pp. 1373–82 (1996); M. S. O'Reilly et al., "Angiostatin: a circulating endothelial cell inhibitor that suppresses angiogenesis and tumor growth," Cold Spring Harb. Symp. Quant. Biol., vol. 59, pp. 471–82 (1994); and J. L. Masferrer et al., "Antiangiogenic and antitumor activities of cyclooxygenase-2 inhibitors," Cancer Res., vol. 60, pp. 1306–11 (2000).

EXAMPLE 9

Effectiveness of LAU-8080 on Other Tumor Types

This compound, referred to as either BN-50730 or LAU-8080, should be useful in treating any tumor that uses bFGF-stimulated angiogensis, including but not limited to, carcinomas of the lung, breast, colon, stomach, pancreas, skin, uterus, cervix, vagina penis, mouth, larnyx, esophagus, liver, kidney or prostate. The compound may also be useful for treating sarcomas, such as soft tissue sarcomas of the muscle or connective tissue, or osteosarcomas. The compound may also be effective against tumors of neurological origin, such as neuroblastomas and glioblastomas and for tumors of neuroectodemal origin such as neuroblastomas. Further, the compound may be effective against metastatic lesions from each of the above tumor types. Because angiogenesis is an important component of the etiology of lymphomas and leukemias in the bone marrow, the compound can also be effective against liquid tumors including, but not limited to, Hodgkin's disease, non-Hodgkin's lymphoma, B-cell lymphomas, T-cell lymphomas, acute lymphocytic leukemia, chronic myloid leukemia, and acute myloid leukemia. Additionally, the compound may be useful for shrinking non-malignant tumors that depend on bFGF-stimulated angiogensis for growth.

The effectiveness of this compound on the above tumor types can be tested by methods known to those of ordinary skill in the art. A representative tumor cell line will be obtained from the ATCC and expanded through serial passage using standard cell culture techniques. Following expansion, the cells will be implanted into the appropriate location in athymic nude (nu/nu) mice. The tumors will be allowed to grow to a volume of about 100 mm³, as determined by the method described above in Example 1. The mice will then be randomized into at least two groups. One group, the control, will receive a placebo injection; the other group will receive daily injections of LAU-8080. The tumors will be measured daily. A significant reduction in the size of tumor in the treated mice group over the control group will indicate that LAU-8080 is effective in this tumor type.

The complete disclosures of all references cited in this specification are hereby incorporated by reference. Also incorporated by reference is the full disclosure of each of the following documents: J. D. Hunt et al., "A Platelet-Activating Factor Antagonist, BN-50730, Inhibits Basic Fibroblast Growth Factor-Induced Human Umbilical Vein Endothelial Cell Proliferation and Tumor Xenograft Expansion in Athymic Nude Mice," submitted to Cancer, on Sep. 27, 2000; and J. D. Hunt et al., "The Platelet-Activating Factor (PAF) Antagonist BN-50730 Inhibits Angiogenesis," Proceedings of the American Association for Cancer Research: Cell and Tumor Biology, vol. 41, abstract 4099 (2000). In the event of an otherwise irreconcilable conflict, however, the present specification shall control.

We claim:

1. A method of inhibiting the growth of a tumor in a mammal, wherein the tumor is a carcinoma of the lung or of the prostate and wherein the growth of the tumor depends on basic fibroblast growth factor-stimulated angiogenesis, said method comprising administering to the mammal a therapeutically effective amount of bFGF-active PAF antagonist tetrahydro-4,7,8,10-methyl-1-(chloro-2-phenyl)-6-(methoxy-4-phenyl-carbomoyl)-9-pyrido[4',3'-4,5] thieno[3,2-f] triazolo-1,2,4-[4,3-a]diazepine-1,4 (BN-50730).

2. The method of claim 1, additionally comprising the step of administering to the mammal another compound that inhibits tumor angiogenesis.

3. The method of claim 2, wherein the additional compound is chosen from a group comprising CV 3988, WEB 2086, INF-2α, TNP-470, endostatin, SU 5416, SU 6668, batimistat, angiostatin, and celecoxib.

4. The method of claim 1, wherein said administering of the bFGF-active PAF antagonist is performed by subcutaneous injection, intravenous injection, intraperitoneal injection, or transdermal absorption.

5. The method of claim 1, wherein the mammal is a human.

6. The method of claim 1, wherein the tumor is a form of carcinoma of the lung.

7. The method of claim 1, wherein the tumor is a form of carcinoma of the prostate.

* * * * *